United States Patent [19]

Jones et al.

[11] Patent Number: 5,344,976
[45] Date of Patent: Sep. 6, 1994

[54] PROCESS FOR REMOVING IODIDE COMPOUNDS FROM CARBOXYLIC ACIDS AND CARBOXYLIC ACID ANHYDRIDES

[75] Inventors: Michael D. Jones, North Humberside; Derrick J. Watson, East Yorkshire; Bruce L. Williams, North Humberside, all of England

[73] Assignees: BP Chemicald Limited; The British Petroleum Company P.L.C., both of London, United Kingdom

[21] Appl. No.: 72,365

[22] Filed: Jun. 3, 1993

Related U.S. Application Data

[63] Continuation of Ser. No. 959,149, Oct. 9, 1992, abandoned.

[30] Foreign Application Priority Data

Oct. 18, 1991 [GB] United Kingdom ............... 9122168

[51] Int. Cl.$^5$ .................. C07C 51/47; C07C 51/573; C07C 53/08
[52] U.S. Cl. ..................................... 562/608; 210/665
[58] Field of Search ...................... 562/608; 210/665

[56] References Cited

U.S. PATENT DOCUMENTS

| | | | |
|---|---|---|---|
| 2,409,441 | 5/1946 | Metzger | 562/608 X |
| 3,732,320 | 5/1976 | Ford | 260/637 R |
| 3,799,977 | 3/1974 | Rutledge | 562/538 |
| 3,969,344 | 3/1976 | Ackermann et al. | 562/608 X |
| 4,007,130 | 2/1977 | Leach et al. | 252/411 R |
| 4,238,294 | 12/1980 | Pasquale | 562/319 |
| 4,269,705 | 5/1981 | Yoshioka et al. | 562/600 |
| 4,487,959 | 12/1984 | Dickerson | 560/248 |
| 4,615,806 | 10/1986 | Hilton | 210/690 |
| 4,894,477 | 1/1990 | Scates et al. | 562/319 |
| 5,124,290 | 6/1992 | Epenbach et al. | 502/12 |

FOREIGN PATENT DOCUMENTS

| | | |
|---|---|---|
| 2012784 | 10/1971 | Denmark . |
| 0087870 | 9/1983 | European Pat. Off. . |
| 0196173 | 10/1986 | European Pat. Off. . |
| 0296584 | 12/1988 | European Pat. Off. . |
| 0482787 | 4/1992 | European Pat. Off. . |
| 0484020 | 5/1992 | European Pat. Off. . |
| 53-101310 | 9/1978 | Japan . |
| 1009950 | 1/1989 | Japan . |
| 1228560 | 9/1989 | Japan . |
| 1253607 | 11/1971 | United Kingdom . |
| 2020257 | 11/1979 | United Kingdom . |
| 2112394 | 7/1983 | United Kingdom . |

OTHER PUBLICATIONS

Amberlyst 15, Technical Bulletin, Rohm & Haas, 1978.
Chemical Processing by Ion Exchange, p. 14, Ion Removed from Glacial Acetic Acid (1978).
Kunin, Amber-Hi-lite, No. 78, Nov. 1963, "Macroreticular Ion Exchange Resins".

*Primary Examiner*—Arthur C. Prescott
*Attorney, Agent, or Firm*—Brooks Haidt Haffner & Delahunty

[57] ABSTRACT

In a process for removing iodide compounds from a liquid composition comprising carboxylic acids having 2 to 6 carbon atoms or anhydrides thereof, by passing the liquid composition through a silver, mercury, palladium and/or rhodium-exchanged strong acid cation exchange resin, prior to contacting with the metal-exchanged resin the composition is contacted with a cation exchanger in the acid form to remove at least a portion of the metal ion contaminants in the liquid composition which have been found to displace the silver, mercury, palladium and/or rhodium from the metal-exchanged resin.

9 Claims, No Drawings

PROCESS FOR REMOVING IODIDE COMPOUNDS FROM CARBOXYLIC ACIDS AND CARBOXYLIC ACID ANHYDRIDES

This application is a continuation, of application Ser. No. 07/959,149, filed Oct. 9, 1992, now abandoned.

The present invention relates to a process for removing iodide compounds, e.g. alkyl iodides and the like, from carboxylic acids and/or carboxylic acid anhydrides. In particular the present invention is suited to purifying acetic acid and/or acetic anhydride prepared by the rhodium catalysed, methyl iodide promoted carbonylation of methanol and/or methyl acetate.

It is known that a problem associated with acetic acid and/or acetic anhydride produced by carbonylation of methanol and/or methyl acetate in the presence of a rhodium/methyl iodide catalyst system is that even after distillation, the acetic acid and/or acetic anhydride frequently contains small amounts of iodide impurities. Whilst the exact nature of these impurities is not known for certain, they probably comprise a mixture of iodide compounds such as methyl iodide and other higher alkyl iodides e.g. hexyl iodide, hydrogen iodide and iodide salts. Such impurities are particularly troublesome since they poison many of the catalysts which are employed in subsequent chemical conversions of the acetic acid and/or acetic anhydride. A case in point are the catalysts used to prepare vinyl acetate from ethylene and acetic acid which are extremely sensitive to iodide impurities.

Several methods of removing iodide impurities from acetic acid and/or acetic anhydride are known. GB-A-2112394, for example, teaches the use of anion exchange resins. EP-A-0196173 describes the removal of iodide impurities from non aqueous organic media such as acetic acid by the use of a silver or mercury containing macroreticular strong acid cation exchange resin such as Amberlyst 15 (Amberlyst is a Registered Trade Mark).

EP-A-2968584 also describes using silver exchanged macroreticular resins to purify acetic acid contaminated with iodide impurities.

It has been found that a problem associated with the use of silver-exchanged strong acid cation exchange resins such as described in EP-A-0196173 is that the silver may be displaced by metals which may be present as contaminants in the carboxylic acid and/or anhydride. This displacement of silver is undesirable as it may result in a lowering of the capacity and/or efficiency of the resin and it may also result in unacceptable product contamination with silver.

The technical problem to be solved therefore is to provide an improved process for the removal of iodide compounds from carboxylic acids and/or carboxylic acid anhydrides.

Thus, according to the present invention there is provided a process for removing iodide compounds from a liquid composition comprising a carboxylic acid having 2 to 6 carbon atoms and/or a corresponding carboxylic acid anhydride thereof, and metal ion contaminants, which process comprises contacting the liquid composition with a metal-exchanged ion exchange resin having strong acid cation exchange sites at least 1% of which are occupied by at least one metal selected from the group consisting of silver, mercury, palladium and rhodium wherein prior to contacting with said metal-exchanged resin, the liquid composition is contacted with a cation exchanger in the acid form to remove at least a portion of the metal ion contaminants.

By using a cation exchanger to remove metal ion contaminants prior to use of a resin having metal-exchanged strong acid cation sites, the displacement of silver, mercury, palladium and/or rhodium from the metal-exchanged sites by the metal ion contaminants is reduced.

The metal ion contaminants in the acid and/or anhydride may arise from corrosion or the use of reagents in the up stream process. Any metal ion capable of displacing silver, mercury palladium and/or rhodium from the metal-exchanged resin should be removed at least in part by the acid-form exchanger. Such metal ions may comprise, for example, at least one of iron, potassium, calcium, manganese and sodium. The metal ion contaminants may be present typically at less than 1 ppm but higher concentrations may be present.

The acid-form cation exchanger reduces the concentration of metal ion contaminants present in the carboxylic acid and/or anhydride to typically less than 100 ppb preferably less than 50 ppb. The concentration to which it is necessary to reduce the metal contaminants depends upon the capacity of the metal-exchanged, iodide removing resin bed to tolerate the residual metal contaminants within its operating life for iodide removal.

Suitable acid-form cation exchangers for removing metal ion contaminants in the present invention may comprise strong acid cation exchange resins for example strong acid macroreticuler resins, for example Amberlyst 15 manufactured by Rohm and Haas; strong acid mesoporous resins, for example Purolite C145 or CT145 manufactured by Purolite and strong acid gel resins, for example IR120A manufactured by Rohm and Haas. Chelating resins and zeolites may also be used.

The liquid composition comprising carboxylic acid and/or anhydride is suitably passed through an acid-form cation exchanger bed at a flow rate sufficient to achieve the desired reduction in metal ion contamination. This flow rate will depend upon such factors as the level of metal ion contamination, the efficiency and capacity of the cation exchanger and the like. Suitably, a flow rate of 1 to 40 bed volumes per hour, preferably 5 to 15 bed volumes per hour may be used.

The temperature of the cation exchanger for metal ion contamination removal should be suitable to maintain the acid and/or anhydride in the liquid state. A suitable operating temperature is in the range 20° to 120° C., preferably 30° to 80° C.

Any suitable pressure may be used for the metal ion contamination removal step.

Metal-exchanged resins suitable for removing iodide compounds in the process of the present invention include metal-exchanged strong acid macroreticuler resins for example Amberlyst 15; metal-exchanged strong acid mesoporous resins for example Purolite C145 or CT145 or Bayer K2411 and metal-exchanged gel resins for example IR120A in which the metal is at least one of silver, mercury, palladium and rhodium.

The metal occupying the at least 1% of the strong acid cation exchange sites of the metal-exchanged, iodide-compound-removing resin of the present invention comprises at least one metal selected from the group consisting of silver, mercury, palladium and rhodium. Preferably the metal is silver.

Operating temperature of the metal-exchanged resin will generally be determined by the operating range of the resin but should be in a range to maintain the acid and/or anhydride in the liquid state, typically 20° to 120° C., preferably 30° to 80° C.

Any suitable pressure may be used for the metal-exchanged resin bed operation.

The liquid composition having reduced metal-ion contamination is suitably passed through a metal-exchanged resin bed at a flow rate sufficient to achieve the desired reduction in iodide compounds. The flow rate of acid and/or anhydride through the metal-exchanged resin bed will depend upon such factors as the level of iodide compound impurity, the efficiency and capacity of the resin and the like. Suitable flow rates are 1 to 40 bed volumes per hour, preferably 5 to 20 bed volumes per hour.

The carboxylic acid used in the process of the present invention may comprise one or more of acetic acid, propionic acid, butyric acid, isobutyric acid, pentanoic acid and hexanoic acid. The carboxylic acid anhydride used in the process of the present invention may comprise one or more anhydrides of acetic acid, propionic acid, butyric acid, isobutyric acid, pentanoic acid and hexanoic acid. Mixed carboxylic acid anhydrides may also be used, for example the mixed anhydride of acetic and propionic acids. Mixtures of carboxylic acids and carboxylic anhydrides may be used.

Preferably the process of the present invention is used for purifying acetic acid and/or acetic anhydride. The process of the present invention is particularly suitable for purifying acetic acid and/or acetic anhydride prepared by the carbonylation of methanol and/or methyl acetate as described, for example in our published European Patent Application EP-A-0087870, the contents of which are hereby incorporated by reference.

The iodide impurities present in the liquid composition comprising carboxylic acid and/or anhydride may be $C_1$ to $C_{10}$ alkyl iodide compounds, hydrogen iodide or iodide salts. The process of the present invention is particularly suitable for removing $C_1$ to $C_{10}$ alkyl iodide compounds such as methyl iodide and hexyl iodide.

The present invention will now be illustrated by reference to the following examples.

Experiment 1 (Comparative Example)

To show the effect of metal ion contaminants on the performance of a silver-exchanged iodide-removing ion exchange resin the following experiment was performed.

A silver-exchanged Purolite C145 ion exchange resin (approximately 35% of cation exchange sites in silver form) was operated at 79° C. with a feed of acetic acid to which had been added hexyl iodide equivalent to a concentration of about 500 ppb iodide and which also contained about 30 ppb iodide equivalent of other unidentified iodide compounds. The feedrate of acetic acid was initially 5 liquid hourly space velocity (LHSV) and then increased to 10 LHSV. Assuming that all the acid was fed at a 10 LHSV, the time on stream before iodide breakthrough was calculated to be 950 hours.

This lifetime is shorter than would be expected from the amount of silver present on the resin. The resin was examined and found to be contaminated with an amount of calcium ion equivalent to an average of 0.7 ppm in the feed. Analysis of silver, calcium and iodide at different positions in the resin bed are given in Table 1. The figures show that silver is moving down the resin bed, as

TABLE 1

| Position in Resin Bed | Concentrations % by weight (figures in bracket mol per kg of resin) | | | Silver Utilisation (1) |
|---|---|---|---|---|
| | Silver | Calcium | Iodide | (%) |
| Top of resin bed (feedpoint) | 6.2 (0.57) | 2.85 (0.70) | 2.5 (0.20) | 35 |
| One third from top | 8.2 (0.76) | 2.05 (0.51) | 1.7 (0.13) | 17.1 |
| Two thirds from top | 14.9 (1.38) | 1.65 (0.41) | 0.6 (0.05) | 3.6 |
| Bottom of resin (outlet) | 13.1 (1.21) | 0.24 (0.06) | 0.1 (0.008) | 0.6 |

(1) defined as iodide concentration/silver concentration × 100% on a molar basis.

calcium accumulates at the top of the resin bed.

Experiment 2

A silver exchanged Bayer K2411 resin (about 35% of cation exchange sites in silver form) was operated at 79° C. with a feed of the same composition as Experiment 1. Acetic acid was fed at a LHSV of 10. For the first 1200 hours of operation the concentration of silver in the acetic acid leaving the bed was <30 ppb. The concentration of silver then steadily increased such that after 1800 hours it was 350 ppb and after 2200 hours it was 700 ppb. After 2200 hours the resin was examined and found to be contaminated with calcium ion equivalent to an average concentration in the feed of 0.6 ppm for the duration of the experiment. Analysis of silver, calcium and iodide at different positions in the resin bed is given in Table 2.

TABLE 2

| Position in Resin Bed | Concentrations % by weight (figures in bracket mol per kg of resin) | | | Silver Utilisation (1) |
|---|---|---|---|---|
| | Silver | Calcium | Iodide | (%) |
| Top of resin bed (feedpoint) | 3.9 (0.36) | 4.9 (1.23) | 2.5 (0.19) | 53 |
| One third from top | 6.9 (0.64) | 3.6 (0.90) | 3.0 (0.24) | 37 |
| Two thirds from top | 13.5 (1.25) | 1.6 (0.40) | 2.4 (0.19) | 15 |
| Bottom of resin (outlet) | 19.0 (1.76) | 0.6 (0.15) | 0.4 (0.03) | 2 |

(1) defined as iodide concentration/silver concentration × 100% on a molar basis.

Again, as in Experiment 1, the silver has migrated down the bed. In this case it has been so severe that unacceptable levels of silver have leached into the liquid acetic acid during the latter part of the Experiment.

Experiment 3

To show the benefits of removing metal ion contaminants from iodide-contaminated acetic acid prior to removing the iodide impurities using a silver-exchanged resin the following experiment was performed.

Acetic acid to which had been added hexyl iodide equivalent to an average of 1105 ppb iodide, 170 ppb iron, 75 ppb potassium and which also contained an average of 430 ppb calcium, (not added) was passed through two sets of resin beds at 79° C. at a LHSV of 10.

Experiment 3A used 30 ml of silver-exchanged Purolite C145 similar to Experiment 1 only and is a comparative experiment.

Experiment 3B used 30 ml of silver-exchanged Purolite C145 similar to Experiment 1 and upstream of this was 30 ml of Purolite C145 in the acid form. This is according to the present invention.

The iodide breakthrough occurred after 5190 hours for Experiment 3A and after 5000 hours for Experiment 3B.

The silver-exchanged resins were analysed for silver, potassium ion and iodide but by a different technique to that used for Experiment 1 which did not allow for calcium determination. The results are shown in Table 3.

The results in Table 3 show that the resin bed in Experiment 3B has less metals than in Experiment 3A such as potassium and iron, these having been removed by the acid-form resin pre-bed. The lifetime of the silver-exchanged resin bed without the acid-form resin bed was comparable with that of the resin bed with the acid-form resin pre-bed because the concentration of metal ion contaminants was rather low, so that the resin bed could accommodate their build-up within the lifetime dictated by its silver loading. Similarly, the distribution of silver within the two resin beds was not significantly affected. Had the metal ion contaminants been present at higher concentrations it is expected that in the absence of the acid-form resin pre-bed they would have had a adverse effect on the lifetime of the silver-exchanged resin bed for iodide compound removal. This is illustrated by the shorter lifetimes of the silver-exchanged resin beds in Experiment 1 compared to those of Experiment 3 (low metal ion contaminants).

TABLE 3

| Position in Resin Bed | Concentration % by weight (figures in brackets mol per kg of resin) | | | | | | | | Silver Utilisation (1) (%) | |
|---|---|---|---|---|---|---|---|---|---|---|
| | Silver | | Potassium | | Iron | | Iodide | | | |
| | 3A | 3B | 3A | 3B | 3A | 3B | 3A | 3B | 3A | 3B |
| Top of bed (feedpoint) | 7.6 (0.70) | 7.7 (0.70) | 0.42 | 0.04 | 1.8 | <0.6 | 6.5 (0.51) | 8.0 (0.63) | 73 | 89 |
| One third from top | 8.0 (0.74) | 8.3 (0.77) | 0.33 | 0.02 | 1.5 | <0.5 | 6.5 (0.51) | 10.6 (0.83) | 69 | 108 |
| Two thirds from top | 7.7 (0.72) | 8.4 (0.78) | 0.32 | 0.02 | 1.2 | <0.5 | 5.9 (0.46) | 5.8 (0.46) | 65 | 59 |
| Bottom of resin bed | 8.5 (0.79) | 9.5 (0.88) | 0.21 | 0.02 | <0.7 | <0.7 | 2.6 (0.21) | 1.0 (0.08) | 26 | 9 |

(1) defined as iodide concentration/silver concentration × 100% on a molar basis

We claim:

1. A process for removing iodide compounds from a liquid composition comprising a carboxylic acid having 2 to 6 carbon atoms or an anhydride thereof, and metal ion contaminants, which process comprises contacting said liquid composition with a metal-exchanged ion exchange resin having strong acid cation exchange sites at least 1% of which are occupied by at least one metal selected from the group consisting of silver, mercury, palladium and rhodium wherein prior to contacting with said metal-exchanged resin, said liquid composition is contacted with a cation exchanger in the acid form to remove at least a portion of said metal ion contaminants.

2. A process as claimed in claim 1 in which said metal-ion contaminants comprise at least one metal ion contaminant selected from the group consisting of iron, potassium, calcium, sodium and manganese.

3. A process as claimed in claim 1 or claim 2 in which said carboxylic acid comprises acetic acid.

4. A process as claimed in claim 1 or claim 2 in which said iodide compounds comprise $C_1$ to $C_{10}$ alkyl iodides.

5. A process as claimed in claim 3 in which said iodide compounds comprise $C_1$ to $C_{10}$ alkyl iodides.

6. A process as claimed claim 1 in which said acid-form cation exchanger comprises at least one resin selected from the group consisting of acid-form strong acid cation exchange macroreticular, mesoporous and gel resins, acid-form chelating resins and acid-form zeolites.

7. A process as claimed in claim 1 in which said metal-exchanged resin comprises at least one resin selected from the group consisting of macroreticular, mesoporous and gel resins.

8. A process as claimed in claim 7 in which at least 1% of the strong acid exchange sites of said metal-exchanged resin are occupied by silver.

9. A process for removing $C_1$ to $C_{10}$ alkyl iodides from a liquid composition comprising acetic acid or an anhydride thereof, $C_1$ to $C_{10}$ alkyl iodides and metal ion contaminants which process comprises the steps of:

(a) passing said liquid composition through a resin bed comprising acid-form strong acid cation exchange resin at a flow rate of 1 to 40 resin bed volumes per hour and at a temperature in the range 20° to 120° C. to remove at least a portion of said metal ion contaminants, and (b) passing the product of step (a) through an ion exchange resin bed comprising an ion exchange resin having strong acid cation exchange sites at least 1% of which are occupied by silver, at a flow rate of 1 to 40 resin bed volumes per hour and at a temperature in the range 20° to 120° C.

* * * * *